US007229462B2

(12) United States Patent
Sutton et al.

(10) Patent No.: US 7,229,462 B2
(45) Date of Patent: Jun. 12, 2007

(54) VASCULAR FILTER SYSTEM FOR CAROTID ENDARTERECTOMY

(75) Inventors: Gregg S. Sutton, Maple Grove, MN (US); Jeffrey Welch, New Hope, MN (US)

(73) Assignee: Angioguard, Inc., Plymouth, MN (US)

( * ) Notice: Subject to any disclaimer, the term of this patent is extended or adjusted under 35 U.S.C. 154(b) by 272 days.

(21) Appl. No.: 10/083,866

(22) Filed: Feb. 26, 2002

(65) Prior Publication Data

US 2002/0091408 A1 Jul. 11, 2002

Related U.S. Application Data

(63) Continuation-in-part of application No. 09/365,146, filed on Jul. 30, 1999.

(51) Int. Cl.
*A61F 2/01* (2006.01)
(52) U.S. Cl. .......................................... 606/200; 604/8
(58) Field of Classification Search ................ 606/200; 604/8, 9
See application file for complete search history.

(56) References Cited

U.S. PATENT DOCUMENTS

| 3,435,824 | A | 4/1969 | Gamponia |
| 3,889,685 | A | 6/1975 | Miller, Jr. et al. |
| 3,952,747 | A | 4/1976 | Kimmell, Jr. |
| 4,230,119 | A | 10/1980 | Blum |
| 4,349,029 | A | 9/1982 | Mott |
| 4,425,908 | A | 1/1984 | Simon |
| 4,494,531 | A | 1/1985 | Gianturco |
| 4,545,390 | A | 10/1985 | Leary |
| 4,619,246 | A | 10/1986 | Molgaard-Nielsen et al. |
| 4,619,274 | A | 10/1986 | Morrison |
| 4,688,553 | A | 8/1987 | Metals |
| 4,706,671 | A | 11/1987 | Weinrib |
| 4,723,549 | A | 2/1988 | Wholey et al. |
| 4,727,873 | A | 3/1988 | Mobin-Uddin |
| 4,781,177 | A | 11/1988 | Lebigot |
| 4,790,812 | A | 12/1988 | Hawkins, Jr. et al. |
| 4,790,813 | A | 12/1988 | Kensey |
| 4,793,348 | A | 12/1988 | Palmaz |
| 4,794,928 | A | 1/1989 | Kletschka |
| 4,832,055 | A | 5/1989 | Palestrant |
| 4,842,579 | A | 6/1989 | Shiber |
| 4,873,978 | A | 10/1989 | Ginsburg |
| 4,884,573 | A | 12/1989 | Wijay et al. |
| 4,921,484 | A | 5/1990 | Hillstead |

(Continued)

FOREIGN PATENT DOCUMENTS

EP  0 737450 A1  10/1996

(Continued)

OTHER PUBLICATIONS

European Search Report for corresponding Applicatio No. EP 03 25 1112, dated May 28, 2003.

(Continued)

*Primary Examiner*—Michael Thaler

(57) ABSTRACT

A removable vascular filter system for capture and retrieval of emboli while allowing continuous perfusion of blood during a carotid endarterectomy procedure, comprising a porous filter membrane with variable diameter holes, and a filter membrane support structure. The system may minimize the incidence of stroke, or other clinical complications that may be associated with carotid endarterectomy procedures.

2 Claims, 6 Drawing Sheets

U.S. PATENT DOCUMENTS

| | | | |
|---|---|---|---|
| 4,926,858 A | 5/1990 | Gifford, III et al. |
| 4,957,501 A | 9/1990 | Lahille et al. |
| 4,969,891 A | 11/1990 | Gewertz |
| 4,990,156 A | 2/1991 | Lefebvre |
| 5,011,488 A | 4/1991 | Ginsburg |
| 5,053,008 A | 10/1991 | Bajaj |
| 5,059,205 A | 10/1991 | El-Nounou et al. |
| 5,092,839 A | 3/1992 | Kipperman |
| 5,095,915 A | 3/1992 | Engelson |
| 5,108,419 A | 4/1992 | Reger et al. |
| 5,133,733 A | 7/1992 | Rasmussen et al. |
| 5,152,777 A | 10/1992 | Goldberg et al. |
| 5,190,540 A | 3/1993 | Lee |
| 5,190,546 A | 3/1993 | Jervis |
| 5,201,757 A | 4/1993 | Heyn et al. |
| 5,242,462 A | 9/1993 | El-Nounou et al. |
| 5,279,546 A | 1/1994 | Mische et al. |
| 5,324,304 A | 6/1994 | Rasmussen |
| 5,329,942 A | 7/1994 | Gunther et al. |
| 5,413,586 A | 5/1995 | Dibie et al. |
| 5,421,832 A | 6/1995 | Lefebvre |
| 5,423,849 A * | 6/1995 | Engelson et al. ........... 606/191 |
| 5,496,277 A | 3/1996 | Termin et al. |
| 5,531,788 A | 7/1996 | Dibie et al. |
| 5,549,626 A | 8/1996 | Miller et al. |
| 5,613,949 A | 3/1997 | Miraki |
| 5,632,760 A | 5/1997 | Sheiban et al. |
| 5,662,631 A | 9/1997 | Marx |
| 5,662,671 A | 9/1997 | Barbut et al. |
| 5,681,347 A | 10/1997 | Cathcart et al. |
| 5,695,519 A | 12/1997 | Summers et al. |
| 5,709,704 A | 1/1998 | Nott et al. |
| 5,749,890 A | 5/1998 | Shaknovich |
| 5,769,816 A | 6/1998 | Barbut et al. |
| 5,779,716 A | 7/1998 | Cano et al. |
| 5,807,398 A | 9/1998 | Shaknovich |
| 5,810,874 A | 9/1998 | Lefebvre |
| 5,814,064 A | 9/1998 | Daniel et al. |
| 5,827,324 A | 10/1998 | Cassell et al. |
| 5,836,969 A | 11/1998 | Kim et al. |
| 5,848,964 A | 12/1998 | Samuels |
| 5,876,367 A | 3/1999 | Kaganov et al. |
| 5,902,263 A | 5/1999 | Patterson et al. |
| 5,910,154 A | 6/1999 | Tsugita et al. |
| 6,001,118 A | 12/1999 | Daniel et al. |
| 6,013,093 A | 1/2000 | Nott et al. |
| 6,051,014 A | 4/2000 | Jang |
| 6,053,932 A | 4/2000 | Daniel et al. |
| 6,059,814 A | 5/2000 | Ladd |
| 6,059,825 A | 5/2000 | Hobbs et al. |
| 6,068,621 A | 5/2000 | Balceta et al. |
| 6,074,357 A | 6/2000 | Kaganov et al. |
| 6,080,178 A | 6/2000 | Meglin |
| 6,126,673 A | 10/2000 | Kim et al. |
| 6,152,946 A | 11/2000 | Broome et al. |
| 6,165,179 A | 12/2000 | Cathcart et al. |
| 6,165,200 A | 12/2000 | Tsugita et al. |
| 6,168,604 B1 | 1/2001 | Cano |
| 6,179,859 B1 | 1/2001 | Bates et al. |
| 6,179,861 B1 | 1/2001 | Khosravi et al. |
| 6,187,015 B1 | 2/2001 | Brenneman |
| 6,203,561 B1 | 3/2001 | Ramee et al. |
| 6,214,025 B1 | 4/2001 | Thistle et al. |
| 6,221,096 B1 | 4/2001 | Aiba et al. |
| 6,241,746 B1 | 6/2001 | Bosma et al. |
| 6,258,115 B1 | 7/2001 | Dubrul |
| 6,267,776 B1 | 7/2001 | O'Connell |
| 6,267,777 B1 | 7/2001 | Bosma et al. |
| 6,270,513 B1 | 8/2001 | Tsugita et al. |
| 6,273,900 B1 | 8/2001 | Nott et al. |
| 6,277,138 B1 | 8/2001 | Levinson et al. |
| 6,280,432 B1 | 8/2001 | Turovskiy et al. |
| 6,290,710 B1 | 9/2001 | Cryer et al. |
| 6,336,934 B1 | 1/2002 | Gilson et al. |
| 6,346,116 B1 | 2/2002 | Brooks et al. |
| 6,726,701 B2 | 4/2004 | Gilson et al. |

FOREIGN PATENT DOCUMENTS

| | | |
|---|---|---|
| EP | 0 791 340 A1 | 8/1997 |
| EP | 1179321 A | 2/2002 |
| FR | 2 652 267 A1 | 3/1991 |
| FR | 2 606 642 A1 | 5/1998 |
| GB | 2020557 A1 | 11/1978 |
| JP | 5-137729 A | 6/1993 |
| JP | 7-88192 A | 4/1995 |
| SU | 764684 A1 | 9/1980 |
| WO | WO 96/01591 A1 | 1/1996 |
| WO | WO 97/17100 A | 5/1997 |
| WO | WO 98/33443 A | 8/1998 |
| WO | WO 98/39053 A | 9/1998 |
| WO | WO 99/23976 A1 | 5/1999 |
| WO | WO 99/58068 A2 | 11/1999 |
| WO | WO 00/16705 A | 3/2000 |
| WO | WO 01/058382 | 8/2001 |
| WO | WO 01/58382 A2 | 8/2001 |
| WO | WO 02/056955 A | 7/2002 |
| WO | WO 02/071920 A | 9/2002 |

OTHER PUBLICATIONS

A. Cragg et al., A New Percutaneous Vena Cava Filter, AJR, 141, Sep. 1983, pp. 601-604.

A. Cragg et al., Nonsurgical Placement of Arterial Endoprosthesis; A New Technique Using Nitinol Wire, AJR, Apr. 1983, p. 261-263.

Eichelter, et al., Prophylaxis of Pulmonary Embolism, Archives of Surgery, vol. 97, Aug. 1968, p. 348 et seq.

G.Lund et al., Long-Term Patency of the Ductus Arteriosus After Balloon Dilatation: An Experimental Study, AJR, Sep. 1983, p. 772.

Greenfield, et al., A New Intercaval Filter Permitting Continued Flow and Resolution of Emboli, Surgery, vol. 73, No. 4, pp. 599-606.

M. H. Wholey et al, PTA and Stents in the Treatment of Extraclavical Circulation, Journal of Advanced Cardiology vol. 9 Suppl. E. 1996, pp. 25E-30E.

Topol, Eric J., et al. Recognition of the Importance of Embolization in Atherosclerotic Vascular Disease American Heart Journal 2000.

* cited by examiner

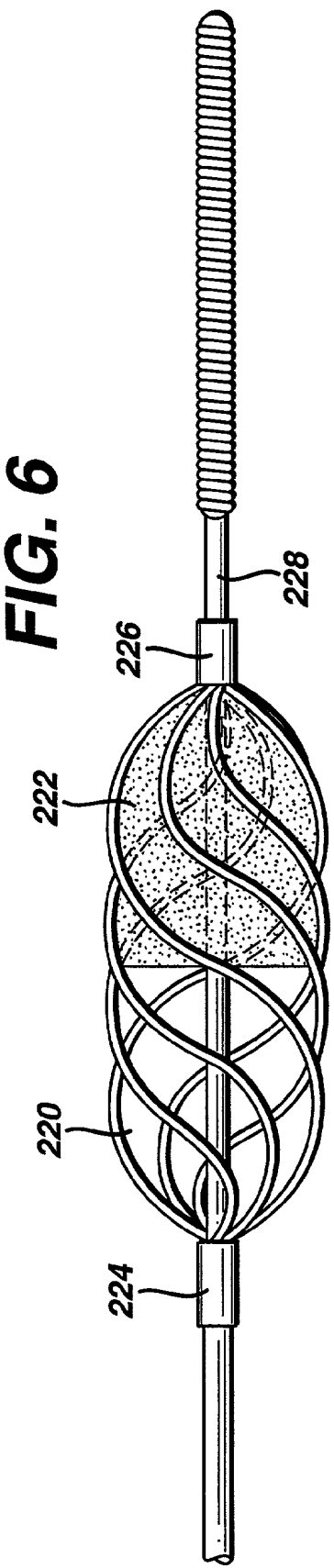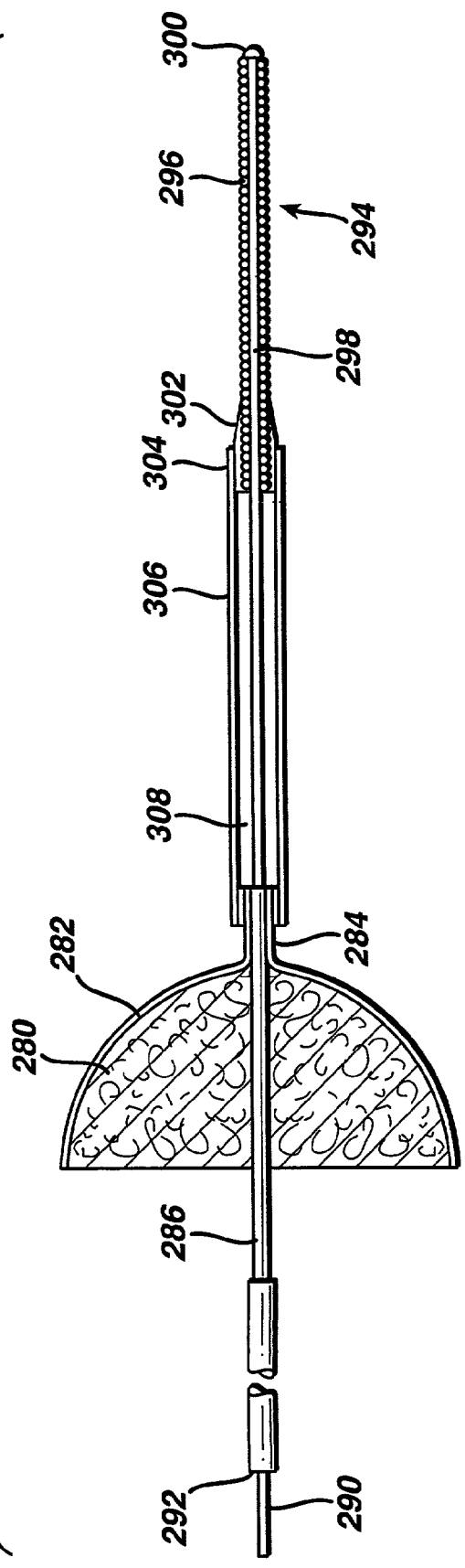

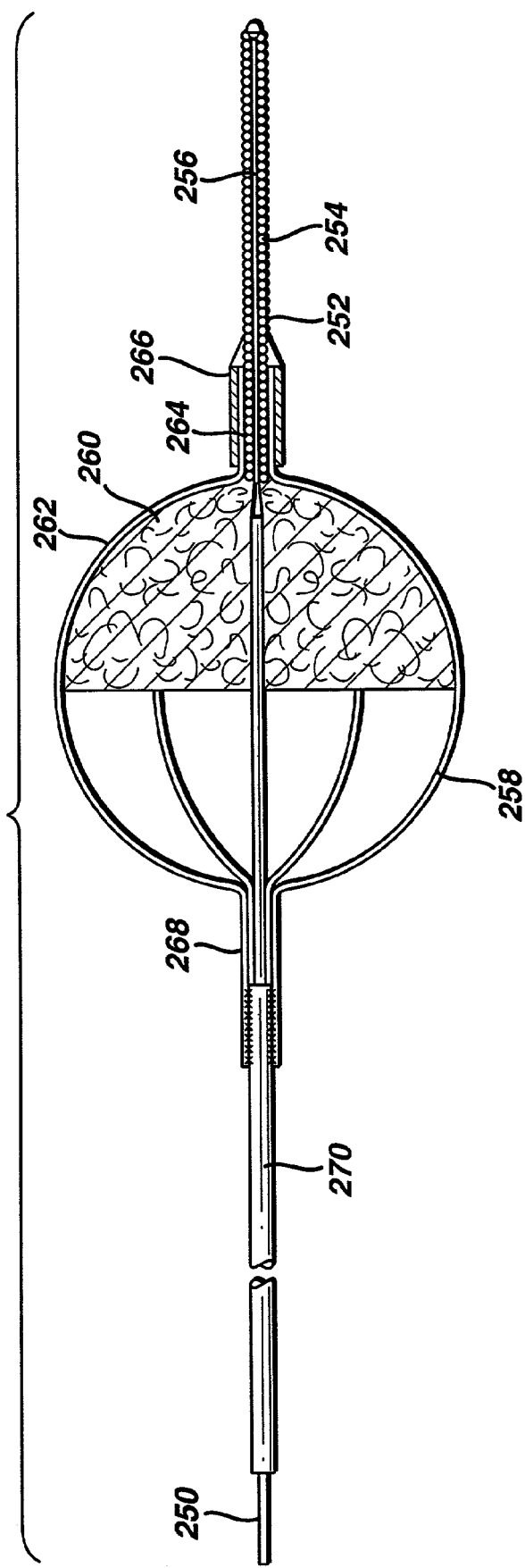

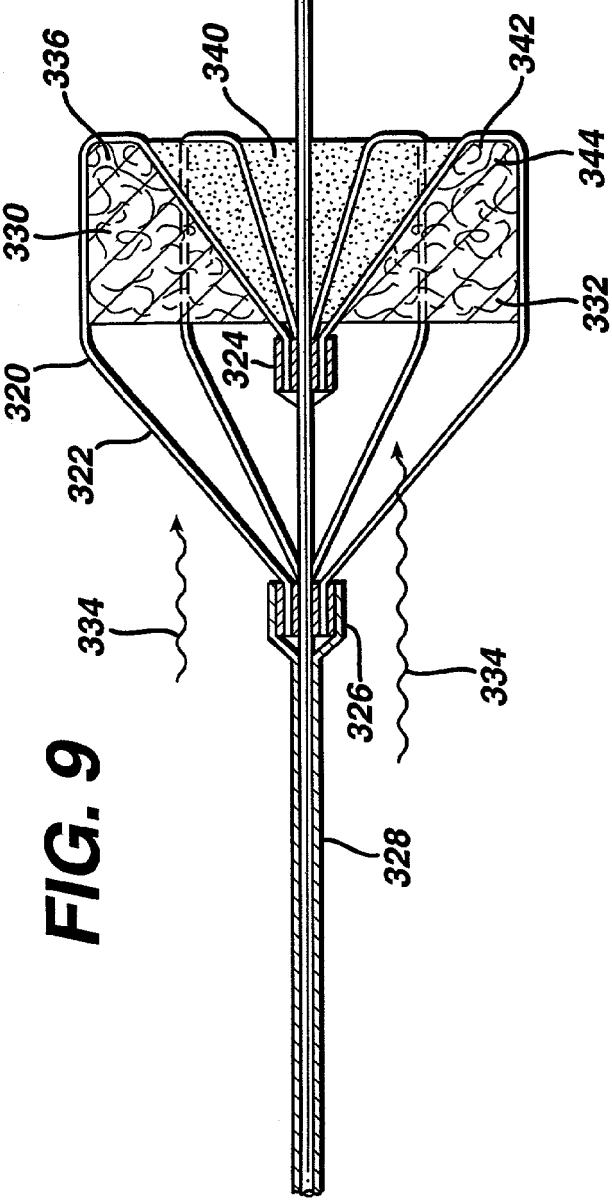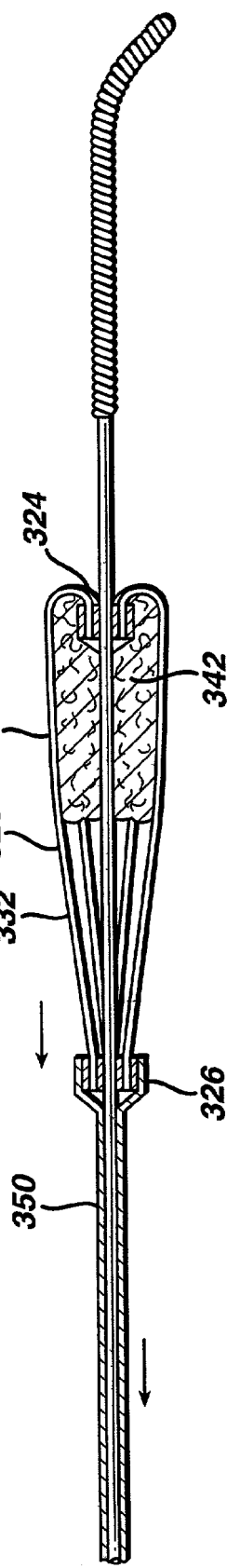
FIG. 9
FIG. 10

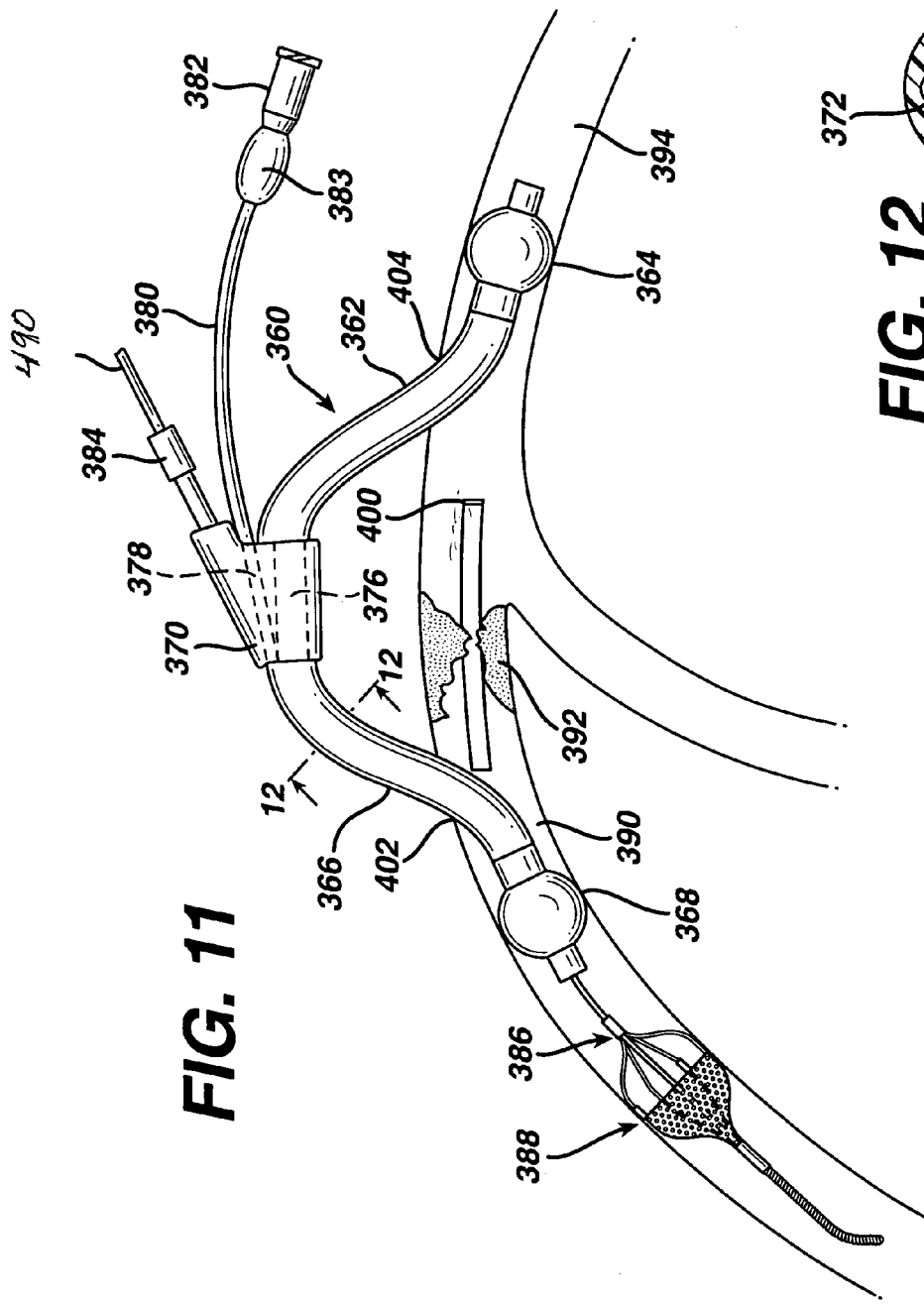
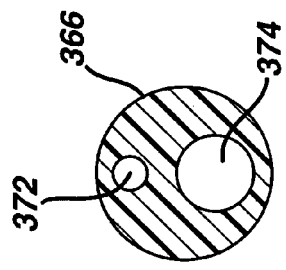

VASCULAR FILTER SYSTEM FOR CAROTID ENDARTERECTOMY

CROSS-REFERENCE TO RELATED APPLICATIONS

This patent application is a continuation-in-part of pending U.S. patent application Ser. No. 09/365,146, filed Jul. 30, 1999, which is incorporated herein by reference.

BACKGROUND OF THE INVENTION

I. Field of the Invention

The present invention relates to the treatment of vascular disease by carotid endarterectomy. More particularly, the present invention relates to a system that reduces macro- and micro-embolization during the carotid endarterectomy procedure.

II. Discussion of the Related Art

A variety of surgical and non-surgical angioplasty procedures have been developed for removing obstructions from blood vessels. Balloon angioplasty utilizes a balloon-tipped catheter, which may be inserted within a stenosed region of the blood vessel. By inflation of the balloon, the stenosed region is dilated. Stenting involves the permanent implantation of a metallic scaffold in the area of the obstruction, following balloon dilatation. The stent is often delivered on an angioplasty balloon, and is deployed when the balloon is inflated. Another alternative is the local delivery of medication via an infusion catheter. Other techniques, such as atherectomy, have also been proposed. In atherectomy, a rotating blade is used to shave plaque from an arterial wall. Surgery involves either removing the plaque from the artery or attaching a graft to the artery so as to bypass the obstructing plaque. In the carotid artery, an arteriotomy is made, and plaque removal, or endarterectomy, is routinely performed.

One problem common to all of these techniques is the potential inadvertent release of portions of the plaque or thrombus, resulting in emboli, which can lodge elsewhere in the vascular system. Such emboli may be dangerous to the patient, and may cause severe impairment of the distal circulatory bed. Depending upon the vessel being treated, this may result in a stroke or myocardial infarction or limb ischemia.

Vascular filters or embolism traps for implantation into the vena cava of a patient are well known, being illustrated by, for example, U.S. Pat. Nos. 4,727,873 and 4,688,533. Additionally, there is a substantial amount of medical literature describing various designs of vascular filters and reporting the results of the clinical and experimental use thereof. See, for example, the article by Eichelter & Schenk entitled "Prophylaxis of Pulmonary Embolism," Archives of Surgery, Vol. 97, August 1968, pp. 348 et seq. See, also, the article by Greenfield, et al., entitled "A New Intracaval Filter Permitting Continued Flow and Resolution of Emboli", Surgery, Vol. 73, No. 4, pp. 599-606 (1973).

Vascular filters are used, often during a postoperative period, when there is a perceived risk of a patient encountering a pulmonary embolus resulting from clots generated at the surgical site. Typically, the filter is mounted in the vena cava to catch large emboli passing from the surgical site to the lungs.

The vascular filters of the prior art are usually permanently implanted in the venous system of the patient, so that even after the need for the filter has abated, the filter remains in place for the lifetime of the patient, absent surgical removal. U.S. Pat. No. 3,952,747 describes a stainless steel filtering device which is permanently implanted transvenously within the inferior vena cava. The filtering device is intended to treat recurrent pulmonary embolism. U.S. Pat. No. 4,873,978 describes a catheter device comprising a catheter body having a strainer mounted at its distal end. The strainer is shiftable between an opened configuration where it extends substantially across the blood vessel to entrap passing emboli, and a closed configuration where it retains the captured emboli during removal of the catheter. A mechanism actuable at the proximate end of the catheter body allows selective opening and closing of the strainer. Typically, the strainer is a collapsible cone having an apex attached to a wire running from the distal end to the proximate end of the catheter body.

Permanent implantation may be deemed medically undesirable, but it has been done because vascular filters are implanted in patients primarily in response to potentially life threatening situations. Accordingly, the potential disadvantages of permanent implantation of a vascular filter are often accepted.

Notwithstanding the usefulness of the above-described methods, a need still exists for an apparatus and method for substantially reducing the risk of embolization associated with carotid endarterectomy. In particular, it would be desirable to provide a device which could be located within the vascular system between the operative site and the brain to collect and retrieve portions of plaque and thrombus which have dislodged during the endarterectomy procedure.

SUMMARY OF THE INVENTION

The present invention provides a vascular filter system which may be used to address the clinical problem of preventing embolization associated with carotid endarterectomy, which may result in a major or minor stroke, as briefly described above.

An objective of the present invention is to provide a vascular filter system for reducing macro- and micro-embolization. Another objective of the present invention is to provide a vascular filter system which is readily removable from the vascular system, or elsewhere, of a patient when the filter is no longer needed. It is a further objective of the present invention to provide a vascular filter system having a configuration which does not require hooks to penetrate and grip the blood vessel walls, so that the implantation results in less blood vessel injury. It is yet a further objective of the invention to capture thrombus or emboli generated during a carotid endarterectomy procedure. It is yet a further objective of the invention to provide a filter membrane with variable-sized holes to allow distal perfusion while capturing embolic particulates.

In one exemplary embodiment, the vascular filter of the present invention comprises a thin membrane attached to a guidewire and supported by fine metal spines. Attachment of the filter membrane to the guidewire allows expansion of the filter membrane with a firm fit inside the artery. The attachment also allows for collapse of the filter membrane at the end of the procedure so that it fits tightly against the guidewire and may be withdrawn through a guide catheter. In another exemplary embodiment, the filter membrane rests upon or is attached to a basket-like structure, at least one end of which is attached to the guidewire. The filter membrane has a hole size such that blood flow is not impeded when the filter membrane is expanded, but micro and macro emboli may be captured. Expansion of the filter membrane is aided by the forward flow of blood against the filter.

In another aspect of the invention, a filter system is useful to capture thrombi or emboli generated during a surgical procedure such as carotid endarterectomy. The system comprises a device having inflatable proximal and distal balloons, wherein a guidewire-based collapsible filter basket extends through a lumen in the distal balloon. The balloons are inflated on either side of a stenosis in a carotid artery to maintain blood flow to the brain through the filter while the stenosis is surgically removed.

An advantage of the present invention is that it provides the benefits of filtration and capture of embolic particulates, temporarily, during a surgical procedure. Another advantage of the present invention is that it provides a filter membrane with variable-sized holes to allow distal perfusion while capturing embolic particulates.

Given the following enabling description of the drawings, the apparatus should become evident to a person of ordinary skill in the art.

BRIEF DESCRIPTION OF THE DRAWINGS

The present invention will be apparent upon consideration of the following detailed description, taken in conjunction with the accompanying drawings, in which the reference characters refer to like parts throughout, and in which:

FIG. 6 illustrates a lateral, cross-sectional view of an alternate basket structure for the exemplary embodiment illustrated in FIG. 1.

FIG. 7 illustrates a lateral, partial cross-sectional view of another exemplary embodiment of the present invention.

FIG. 8 illustrates a lateral, partial cross-sectional view of a further exemplary embodiment of the present invention.

FIG. 9 illustrates a schematic, partial cross-sectional view of another exemplary embodiment of the present invention where the distal section of the filter basket is inverted.

FIG. 10 illustrates a schematic, partial cross-sectional view of the exemplary embodiment illustrated in FIG. 9 where the filter basket is collapsed.

FIG. 11 illustrates a schematic partial cross-sectional view of a filter system in situ in accordance with the present invention.

FIG. 12 illustrates cross-sectional view along line 12—12 as illustrated in FIG. 11.

DETAILED DESCRIPTION OF THE PREFERRED EMBODIMENTS

The present invention relates to a vascular filter system for use in carotid endarterectomy, which may substantially reduce the risk of distal embolization during surgical procedures, while still allowing perfusion of distal tissue.

The system comprises a thin, porous filter membrane with variable-sized openings which is capable of blocking emboli and which is attached to the distal end of a guidewire. In one exemplary embodiment of the invention, a thin, flexible, perforated membrane is supported by four or more supports that form a distally extending basket. At least one end of the basket is attached to the guidewire, and the other, slidable end may be moved to cause the membrane to open or close.

Figure 1:
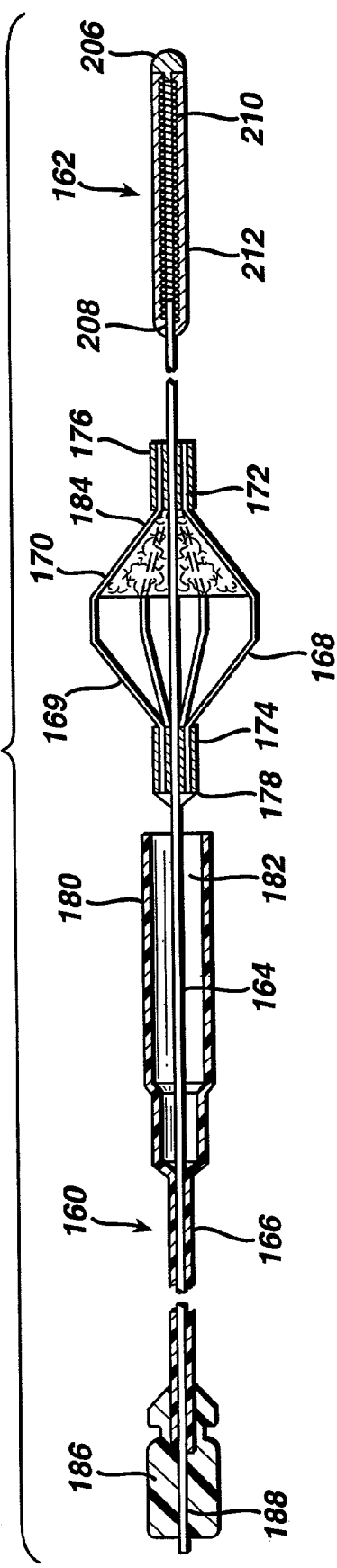
FIG. 1 illustrates a lateral, partial cross-sectional view of one exemplary embodiment of the present invention with the filter membrane in an open position.

The present invention may be better appreciated by reference to the drawings. FIG. 1 illustrates a lateral, cross-sectional view of a distal end of a guidewire 160 with a filter membrane 170 attached thereto. FIG. 1 shows guidewire 160 with a shapeable soft "floppy" tip 162 at its extreme distal end which provides flexibility and maneuverability to guidewire 160. The filter membrane 170 in FIG. 1 is illustrated in an open position.

Guidewire 160 comprises a core wire 164, which extends into floppy tip 162, and a sheath 166. Filter membrane 170 is supported by a basket 169 comprising two or more filter basket wires 168, having distal ends 172 and proximal ends 174. The distal ends 172 of basket wires 168 are fixedly attached by distal radiopaque marker or crimp band 176 to core wire 164, and the proximal ends 174 of basket wires 168 are attached to proximal radiopaque marker or crimp band 178, which is slidable over core wire 164, optionally with a polymeric, such as polyimide, or metallic sleeve between core wire 164 and proximal ends 174. Preferably, proximal marker 178 is fixedly attached to core wire 164, and distal marker 176, with a polymeric or metallic sleeve, is slidable over core wire 164.

The flow of blood in FIG. 1 is toward the distal end of guidewire 160. As such, the force of the flow of blood pushes on deployed filter membrane 170 and helps to maintain filter membrane 170 in the deployed position.

A sheath member 180 is attached to the distal end of sheath 166, sheath member 180 having a lumen 182 with a diameter and length sufficient to receive or slide over proximal marker 178. Sheath 166 and sheath member 180 can be either separate pieces bonded together or a continuous, integral structure. Sheath 166 and sheath member 180 are each made from low friction polymeric material, preferably polytetrafluoroethylene, polyethylene, nylon, or polyurethane.

Filter membrane 170 may comprise a number of different metallic and non-metallic permeable membranes having sufficient porosity to facilitate blood flow but having sufficiently small openings to capture emboli. Filter membrane 170 is preferably affixed at least at its distal portion 184 to core wire 164 and/or basket wire distal ends 172 and, optionally, to basket wires 168. The remainder of filter membrane 170 may be unattached or, preferably, attached to basket wires 168, such as by a suitable adhesive. Preferably basket wires 168 are encapsulated in membrane 170.

Basket 169 may be somewhat cylindrical in its middle with tapered, conical, proximal and distal portions. Alternately, basket 169 may be slightly spherical, optionally with a flat, cylindrical middle portion. Preferably, basket 169 is from about five to about forty mm in length and from about two to about thirty mm, or from about two to about twenty mm, in diameter at its widest.

The proximal end of the sheath 180 is attached to a control handle or guidewire torquer 186. Control handle 186 has an opening 188 for core wire 164 so that sheath 180 can move slidably over core wire 164. For example, when sheath 180 is moved distally toward basket wires 168, filter membrane 170 collapses. Also, there may be instances where sheath 180 will be removed proximally so that other catheters or other vascular devices can be introduced over core wire 164.

Control handle 186, which functions as a torque device, also primarily functions to lock sheath 180 to core wire 164 during insertion.

There are a number of known, commercially available guidewire torquers that may be modified to function as control handle 186. Modification includes, but is not limited to, providing a slightly larger central lumen.

Figure 2:
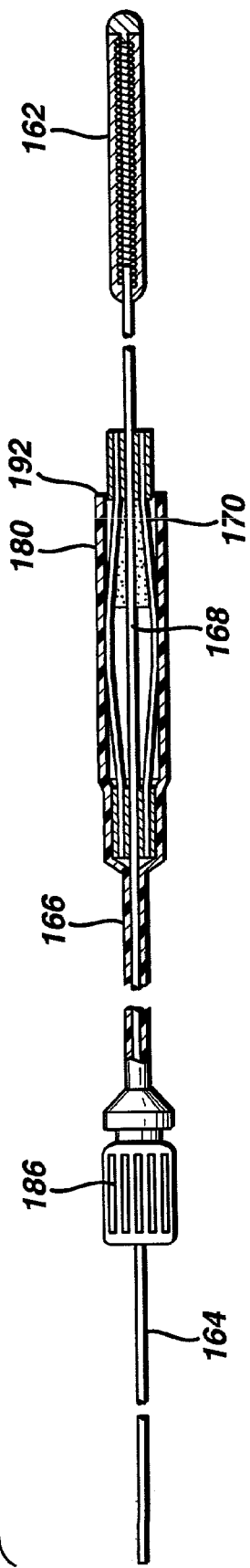
FIG. 2 illustrates a lateral, partial cross-sectional view of the exemplary embodiment of the present invention illustrated in FIG. 1 with the sheath closed.

In FIG. 2 sheath 166 and sheath member 180 are shown advanced distally so that basket wires 168 and filter member 170 are collapsed against core wire 164. The distal end 192 of sheath member 180 may optionally be slightly tapered to provide a better profile for insertion.

Figure 3:
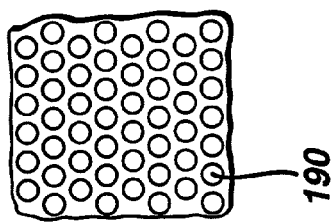
FIG. 3 illustrates a schematic representation of a portion of a filter membrane in accordance with the present invention.

In an exemplary embodiment of the present invention, as shown in FIG. 3, filter membrane 170 comprises a polymeric material such as polyurethane or silicone elastomer that has openings or holes 190 that vary in diameter with one another. Alternately, the filter membrane may comprise fabric or non-fabric meshes, such as those used in known hemodialysis filters or heart-lung bypass machine filters. Suitable materials include polymers or physiologically acceptable metals or alloys. The openings or holes 190 may be created in the material through a laser drilling or other suitable process, or they may be naturally-occurring openings or holes in the material itself.

Holes 190 of filter membrane 170, a pattern for which can be seen in FIG. 3, are preferably only on the conical portion of filter membrane 170. The holes 190 may be from about twenty to about three hundred microns in diameter, and may vary in diameter as compared with one another. The holes 190 may also comprise fibers attached to the circumference of the holes 190, which can serve to increase embolic capture. The vertical row separation of holes 190 may be from about 1.2 to 1.4 times the hole diameter and the center-to-center diameter of holes 190 may be from about 1.4 to 1.6 times the hole diameter, or in an exemplary embodiment the vertical and horizontal spacing of the holes is such that the center-to-center spacing of the holes is from about 1.2 to 2.0 times the hole diameter. Preferably the open area of the holes represents from about ten to fifty percent, more preferably from about ten to forty percent of the filter surface. Alternatively, the holes may be non-uniformly spaced. The mesh should have holes of a size sufficient to block and capture any micro- and macro-emboli which may flow downstream from the site where the stenosis or other problem is being treated, but large enough such that blood flow is not substantially impeded. The mesh used in the filter device of the present invention can have a hole size of from about twenty to about three hundred microns, preferably from about fifty to about one hundred fifty microns. Moreover, the size of filter membrane 170 is such as to allow a firm fit between filter membrane 170 and an artery wall. The diameter of filter membrane 170 will be directly related to the artery being treated, with typical diameters ranging from about two millimeters to about forty millimeters, most preferably from about two millimeters to about twenty millimeters.

Referring back to FIGS. 1 and 2, basket wires 168 may comprise a suitable, physiologically acceptable metal. Stainless steel or nitinol are preferred, although titanium or other metal alloys could be used.

Figure 4:
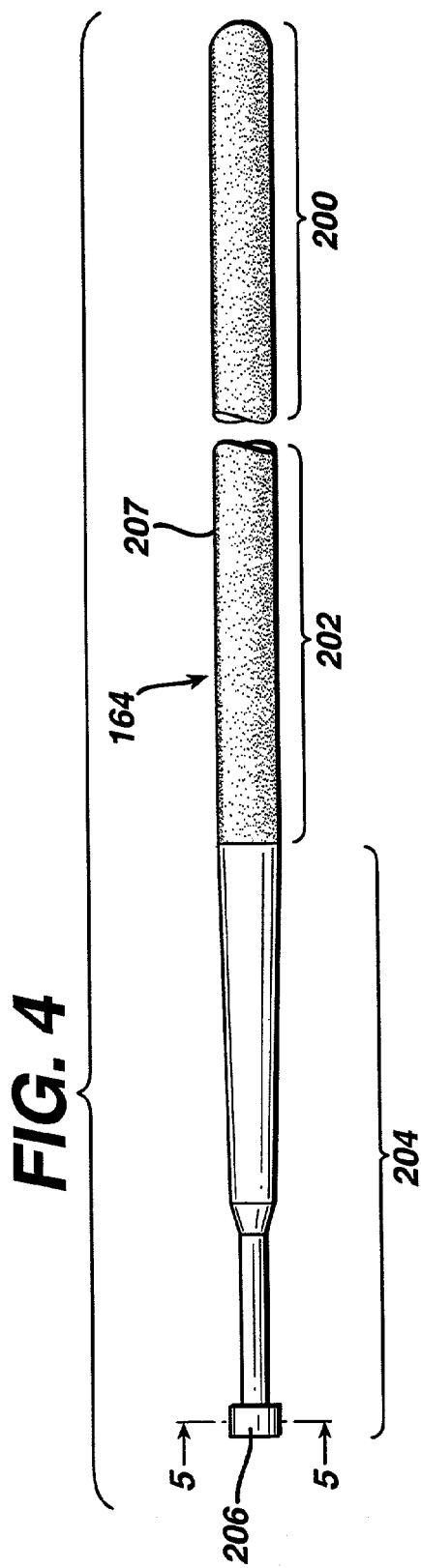
FIG. 4 illustrates a lateral view of a core wire in accordance with the present invention.
Figure 5:
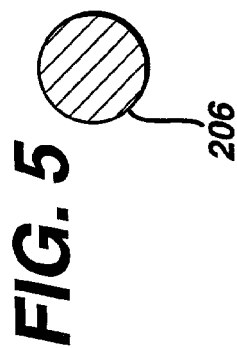
FIG. 5 illustrates a cross-sectional view across section line 5—5 of a portion of the core wire as illustrated in FIG. 4.

Core wire 164, illustrated in greater detail in FIG. 4, where the proximal and middle portions 200 and 202 are substantially uniform in diameter, and then the distal portion 204 tapers to an end point 206. In fact, distal portion 204 could taper uniformly or, more preferably, non-uniformly, as shown in FIG. 4. Typically core wire 164 is from about two hundred fifty to three hundred centimeters in length, with an initial diameter of from about 0.009 to 0.038 inches, preferably from about 0.014 to 0.018 inches. Distal section 204 is typically from about eight to ten centimeters. With a diameter that tapers from about 0.001 to about 0.005 inches, core wire 164 may optionally have a thin polymeric coating 207 for friction reduction. Preferably end point 206 is a solid, squat cylinder, as shown in FIGS. 4 and 5.

Referring back to FIG. 1, floppy tip 162 preferably comprises a radiopaque helical spring 210 that is fixedly attached, e.g., by welding, brazing, or soldering, to end point 206 and, optionally, attachment point 208. Optionally, spring coil 210 may have a polymeric or lubricious coating 212.

FIG. 6 represents an alternate design of the filter system of the present invention, where basket wires 220 are substantially helical in shape. Filter member 222 covers or encompasses the distal portion of basket wires 220, and the proximal and distal portions of basket wires 220 are secured by proximal radiopaque marker or crimp band 224 and distal radiopaque marker or crimp band 226, respectively. Markers 224 and 226 are fixed or slidable on core wire 228 as described above. Preferably there are from four to eight basket wires 220, each with a rotation of from about forty-five degrees to three hundred sixty degrees.

Additional exemplary embodiments of the present invention are illustrated in FIGS. 7 and 8. The schematic representation in FIG. 7 depicts a filter membrane 280 supported by strut wires 282. The distal ends 284 of strut wires 282 are attached to the distal portion of a tubular member 286. A movable core wire 290 extends through a lumen 292 in tubular member 286 to a distal floppy section 294, where a helical spring coil 296 surrounds the distal portion 298 of core wire 290 and is attached to end point 300. There is an attachment point 302 of weld or solder or other suitable material at the proximal portion of spring coil 296 where the distal portion 304 of sheath member 306 is also attached to core wire 290. A lumen 308 of sheath member 306 is large enough so that as core wire 290 is pulled proximally, or tubular member 286 is advanced distally, the distal ends 284 of strut wires 282 move into lumen 308 and collapse filter membrane 280.

Moveable core wire 250 of the structure shown in FIG. 8 comprises a floppy tip 252 where a helical spring coil 254 encompasses the distal portion 256 of core wire 250. A basket wire structure component of two or more basket wires 258 supports a filter membrane 260 on the distal portion 262 of the basket structure. Distal ends 264 of the basket wires 258 are encompassed by a radiopaque marker or crimp band 266 that is attached to core wire 250 and/or spring coil 254. The proximal ends 268 of basket wires 258 are attached to the distal portion of a sheath 270 that surrounds core wire 250. Sheath 270 moves slidably over core wire 250 so that when sheath 270 is pulled proximally into core wire 250, filter membrane 250 collapses.

In FIG. 9, a basket 320 comprising from four to eight strut wires 322 is secured by a distal fixed grommet 324 and a proximal slidable grommet 326. Grommet 326 is slidable over core wire 328. Filter membrane 330 is attached to or arranged upon basket 320, with a proximal section 332 of the membrane 330 being open to flow, represented by arrows 334. A distal portion 336 of membrane 330 forms a conical shape 340 that extends proximally. The filter may be deployed by, for example, a sheath or a tube fixed to the proximal slidable grommet 326. This design is optimized for perfusion and emboli collection. For example, as more emboli is collected, it tends to collect in outer, non-filter areas, leaving the holes open for perfusion.

Membrane 330 preferably has holes only in distal section 336/340, which holes are arranged as described above. It is believed that under normal, substantially laminar flow conditions, debris or emboli 342 will tend to collect in annular recesses 344.

To close and capture emboli, as shown in FIG. 10, slidable grommet 326 is moved proximally to collapse basket 320 and membrane 330. This may be accomplished with, for example, sheath 350 or a fixed tubular member or other apparatus that is preferably slidable over the core wire.

The wires, membrane, and other materials of this exemplary embodiment are consistent with those described above.

In the exemplary embodiment of the invention shown in FIG. 11, a filter system 360 comprises a proximal section 362 having a proximal balloon 364, a distal section 366 having a distal balloon 368, and a middle connecting section 370. Each of proximal section 362 and distal section 366 has at least two lumens, one for inflation of a balloon and one for blood flow. See, for example, the cross section of FIG. 12, wherein distal section 366 has inflation lumen 372 and blood flow lumen 374.

Middle section 370 comprises a lumen 376 to connect the blood flow lumen of proximal section 362 and distal section 366, as well as lumen 378 to connect to respective inflation lumens. Lumen 378 is in turn in fluid connection through inflation catheter 380 with an inflation hub 382, which in turn can be connected to known inflation means. Inflation hub 382 may have an inflation cuff 383 to assist the operator in determining or monitoring the extent of inflation. Middle section 370 also has a port 384 for insertion or removal of a guidewire-based filter 386 with filter basket 388. The proximal end of guidewire 490 extends proximal from port 384.

In the exemplary embodiment described above, the vascular filter system is advanced through blood flow lumen 374 of distal section 366. It is within the scope of the present invention that distal section 366 may comprise an additional lumen through which the vascular filter system would be advanced.

It is within the scope of the present invention that there may be an additional member with an inflatable balloon and lumen in fluid connection with the middle section. The additional member would have a lumen for insertion of a vascular filter through a port in the middle section. This arrangement would facilitate placing balloons and vascular filters in the internal and external carotid arteries.

During a carotid endarterectomy, filter system 360 is positioned prior to the surgical procedure. First, an incision 402 would be made in the internal carotid artery 390 distal to a stenosis 392 and distal section 366 would be inserted through the incision, with distal balloon 368 in deflated condition. Next, proximal section 362 with balloon 364 deflated would be inserted into an incision 404 in the common carotid artery 394. Then, balloons 364 and 368 would be inflated essentially simultaneously (although optionally the apparatus could be configured for separate inflation). Once the balloons are inflated, an incision 400 is made adjacent stenosis 392. Vascular filter 386 may be inserted either with filter system 360 or later, preferably prior to incision 400.

Subsequent to this procedure, after incision 400 has been closed, balloons 364 and 368 are deflated. Then, filter basket 388 would be collapsed and withdrawn proximally through port 384.

The preceding specific exemplary embodiments are illustrative of the practice of the invention. It is to be understood, however, that other expedients known to those skilled in the art or disclosed herein, may be employed without departing from the spirit of the invention or the scope of the appended claims.

What is claimed is:

1. A filter system for carotid endarterectomy comprising:
proximal and distal members each having at least first and second lumens, and an inflatable balloon and each first lumen being in fluid communication with the respective inflatable balloon;
a middle section positioned between the proximal and distal members, the middle section having a third lumen in fluid communication with each of the second lumens, a fourth lumen in fluid communication with each of the first lumens and a first inflation port, and a fifth lumen in fluid communication with a second port; and
a vascular filter system comprising a guidewire insertable into the second port and advanced through the second lumen of the distal member, wherein each of the the inflatable balloons is capable of being inflated simultaneously, the vascular filter system comprising (a) a filter membrane support structure, and (b) a filter membrane attached to the filter membrane support structure, the filter membrane having holes, wherein the holes comprise varying diameters ranging from about 20 to about 300 microns, and (c) one or more fibers affixed to the circumference of the holes and configured to capture embolic material.

2. The filter system of claim 1 wherein said holes are non-uniformly spaced.

* * * * *